(12) United States Patent
Nakano et al.

(10) Patent No.: US 8,979,743 B2
(45) Date of Patent: Mar. 17, 2015

(54) ENDOSCOPE DEVICE AND ENDOSCOPIC IMAGE DISTORTION CORRECTION METHOD

(75) Inventors: Sumito Nakano, Tokyo (JP); Fumio Hori, Tokyo (JP); Kiyotomi Ogawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 2018 days.

(21) Appl. No.: 12/168,242

(22) Filed: Jul. 7, 2008

(65) Prior Publication Data
US 2010/0004507 A1 Jan. 7, 2010

(51) Int. Cl.
*A61B 1/06* (2006.01)
*A61B 1/00* (2006.01)

(52) U.S. Cl.
CPC ........... *A61B 1/00126* (2013.01); *A61B 1/0014* (2013.01)
USPC ........... 600/172; 600/109; 600/118; 600/160; 600/175; 348/72; 348/74; 348/241

(58) Field of Classification Search
USPC ......... 600/112, 103, 109, 118, 160, 172, 175; 348/72, 74, 241
See application file for complete search history.

(56) References Cited

U.S. PATENT DOCUMENTS

| 5,784,098 | A | 7/1998 | Shoji et al. | |
|---|---|---|---|---|
| 6,063,023 | A | 5/2000 | Sakiyama et al. | |
| 6,816,187 | B1 * | 11/2004 | Iwai et al. | 348/187 |
| 6,937,268 | B2 | 8/2005 | Ogawa | |
| 2002/0183590 | A1 * | 12/2002 | Ogawa | 600/117 |
| 2002/0191076 | A1 * | 12/2002 | Wada et al. | 348/78 |
| 2003/0060681 | A1 * | 3/2003 | Yokota | 600/117 |
| 2004/0030221 | A1 * | 2/2004 | Ogawa | 600/175 |

(Continued)

FOREIGN PATENT DOCUMENTS

| JP | 09-061132 A | 3/1997 |
|---|---|---|
| JP | 10-248806 A | 9/1998 |

(Continued)

OTHER PUBLICATIONS

Machine Translation and Drawings of JP2005-279054.*

(Continued)

*Primary Examiner* — John P Leubecker
*Assistant Examiner* — Arnaldo Torres Diaz
(74) *Attorney, Agent, or Firm* — Holtz, Holtz, Goodman & Chick PC (57) ABSTRACT

The present invention is an endoscope device in which a portion of the optical system can be changed using an optical adaptor, provided with: an image pickup member for capturing an image that is input from an optical system that incorporates a reference scope or user scope, and an optical adaptor; a first recording medium that records a first information that includes at least distortion parameters of the reference scope which indicate the optical properties of the reference scope; a second recording medium that records a second information that includes at least distortion parameters of the user scope which indicate the optical properties of the user scope; and a distortion correcting member that corrects distortion in the image captured by the image pickup member when the user scope and the optical adaptor are combined, based on the first information which is read out from the first recording medium and the second information which is read out from the second recording medium.

14 Claims, 10 Drawing Sheets

(56) References Cited

U.S. PATENT DOCUMENTS

| | | |
|---|---|---|
| 2004/0054256 A1* | 3/2004 | Ogawa .......................... 600/118 |
| 2005/0014996 A1 | 1/2005 | Konomura et al. |
| 2006/0176321 A1* | 8/2006 | Nakano et al. ................ 345/660 |
| 2006/0178561 A1* | 8/2006 | Nakano et al. ................ 600/117 |
| 2006/0268257 A1* | 11/2006 | Ogawa ........................ 356/3.13 |
| 2007/0049802 A1* | 3/2007 | Yokota ......................... 600/175 |
| 2007/0167673 A1* | 7/2007 | Enomoto ...................... 600/101 |
| 2008/0015412 A1* | 1/2008 | Hori ............................. 600/109 |

FOREIGN PATENT DOCUMENTS

| | | |
|---|---|---|
| JP | 2001-075019 A | 3/2001 |
| JP | 2003-070719 A | 3/2003 |
| JP | 2003-075136 A | 3/2003 |
| JP | 2004-49638 A | 2/2004 |
| JP | 2004-275359 A | 10/2004 |
| JP | 2004-313241 A | 11/2004 |
| JP | 2005-279054 A | 10/2005 |

OTHER PUBLICATIONS

Japanese Office Action dated Nov. 15, 2011 (and English translation thereof) in counterpart Japanese Application No. 2006-314336.

Japanese Office Action dated Feb. 21, 2012 (and English translation thereof) in counterpart Japanese Application No. 2006-314335.

* cited by examiner

ENDOSCOPE DEVICE AND ENDOSCOPIC IMAGE DISTORTION CORRECTION METHOD

BACKGROUND OF THE INVENTION

1. Field of the Invention

The present invention concerns an endoscope device in which the optical system can be changed using an optical adaptor, and relates to an endoscope device and endoscopic image distortion correction method in which the distortion in the endoscopic image is corrected prior to carrying out measurements.

2. Description of Related Art

Distortion in an endoscopic image arises due to the distortion in an optical system that incorporates an endoscope and an optical adaptor. In the case of conventional endoscope devices, a technique has been proposed in which the endoscope's distortion correcting means corrects image distortion based on optical data that includes distortion correction parameters (see Japanese Patent Application, First Publication No. 2004-049638, for example). Optical data are created by an image processing device during the production process for the optical adaptor, when the optical adaptor and a reference scope are combined. This optical adaptor and optical data are used together with the user scope. Note that measurements employ the images which have been corrected for distortion, thus, measurement precision improves with more accurate distortion correction.

Optical properties (such as magnification, for example) will differ between the reference scope and the user scope. Since the optical data is created when the optical adaptor is combined with the reference scope, it does not reflect the properties of the user scope. Accordingly, distortion correction can be more accurately performed by correcting the distortions that arise due to differences in the properties of the reference and user scopes.

SUMMARY OF THE INVENTION

The present invention is an endoscope device in which a portion of the optical system can be changed using an optical adaptor, provided with:

an image pickup member for capturing an image that is input from an optical system that incorporates a reference scope or user scope, and an optical adaptor;

a first recording medium that records a first information that includes at least distortion parameters of the reference scope which indicate the optical properties of the reference scope;

a second recording medium that records a second information that includes at least distortion parameters of the user scope which indicate the optical properties of the user scope; and a distortion correcting member that corrects distortion in the image captured by the image pickup member when the user scope and the optical adaptor are combined, based on the first information which is read out from the first recording medium and the second information which is read out from the second recording medium.

In the invention described above, the first recording medium is detachable, and may also record as the first information, the optical data for correcting distortion in an optical system incorporating the reference scope and the optical adaptor.

In the invention described above, the first recording medium is detachable, and may also record as the first information, the optical data for correcting distortion in the optical system of the optical adaptor.

In the invention described above, the first recording medium may record a first recognition information for recognizing at least the reference scope, so that the distortion parameters of the reference scope can be referenced from other recording medium.

In the invention described above, the second recording medium may be provided inside the endoscope device, or may be provided to an internal part of the endoscope that can be released from the endoscope device.

In the invention described above, the second recording medium may be a semiconductor memory in which the distortion parameters of at least the user scope are recorded.

In the invention described above, the second recording medium may be a medium in which the distortion parameters of at least the user scope are printed or copied to permit recognition.

In the invention described above, the second recording medium may record the second recognition information for recognizing at least the user scope, so that the distortion parameters of the user scope can be referenced from other recording medium.

Further, the present invention is an endoscopic image distortion correction method for correcting the distortion in an image captured by an endoscope device in which it is possible to change a portion of the optical system using an optical adaptor, the method including:

a step for obtaining a first information which includes at least distortion parameters of the reference scope which indicate the optical properties of the reference scope, from image data in which a specific target is captured when the optical adaptor is not attached to the reference scope;

a step for recording the first information in the first recording medium;

a step for obtaining the second information which includes at least distortion parameters of the user scope which indicate the optical properties of the user scope, from image data in which a specific target is captured when the optical adaptor is not attached to the user scope;

a step for recording the second information in the second recording medium; and a step for correcting the distortion in the image captured when the optical adaptor is attached to the user scope, based on the first information read out from the first recording medium and the second information read out from the second recording medium.

The present invention is an endoscope device in which a portion of the optical system can be changed using an optical adaptor, provided with:

an image pickup member for capturing an image that is input from an optical system that incorporates a reference scope or a user scope, and an optical adaptor; and a distortion correcting member that corrects distortion in the image captured by the image pickup member when the user scope and the optical adaptor are combined, based on the optical data for correcting distortion in an optical system that incorporates a reference scope and the optical adaptor, distortion parameters of the reference scope which indicate the optical properties of the reference scope, and distortion parameters of the user scope which indicate the optical properties of the user scope.

In the invention described above, a measuring member may also be provided for measuring an object based on the image which has been corrected for distortion by the correcting member.

In the invention described above, the optical adaptor may be provided with an optical element for performing image pickup from different viewpoints using the image pickup member, and the measuring member may perform three-dimensional measurements using triangulation of the image captured from different viewpoints by the image pickup member via the optical element.

In the invention described above, the optical element may have a plurality of optical paths.

In the invention described above, the distortion parameters of the reference scope and the distortion parameters of the user scope may each include the magnifications for the respective scopes.

In the invention described above, the distortion parameters of the reference scope and the distortion parameters of the user scope may include the distortion centers for the respective scopes.

The present invention is an endoscope device in which a portion of the optical system can be changed using an optical adaptor, provided with:

an image pickup member for capturing an image that is input via an optical system that incorporates a reference scope or a user scope, and an optical adaptor; and a distortion correcting member that corrects distortion in the image captured by the image pickup member when the user scope and the optical adaptor are combined, based on the optical data for correcting distortion in the optical system of the optical adaptor, and distortion parameters of the user scope which indicate the optical properties of the user scope.

Further, the present invention is an endoscopic image distortion correction method for correcting the distortion in an image captured by an endoscope device in which a portion of the optical system can be changed by the optical adaptor, this method including:

a first step of reading in optical data for correcting distortion in an optical system that incorporates the reference scope and the optical adaptor;

a second step of reading in distortion parameters of the reference scope which indicate the characteristic properties of the reference scope;

a third step of reading in distortion parameters of the user scope which indicate the optical properties of the user scope; and a fourth step of correcting the distortion in the image captured by the image pickup member when the user scope and the optical adaptor are combined, based on the optical data for correcting distortion in the optical system that incorporates the reference scope and the optical adaptor, the distortion parameters of the reference scope which indicate the optical properties of the reference scope, and the distortion parameters of the user scope which indicate the optical properties of the user scope.

In the above invention, the fourth step described above may include processing to correct distortion in the captured image based only on optical data, for the case where reading in of the parameters in step 2 or step 3 has failed.

DETAILED DESCRIPTION OF THE INVENTION

The endoscope device according to the first embodiment of the present invention will now be explained with reference to the figures.

A. First Embodiment

Figure 1:
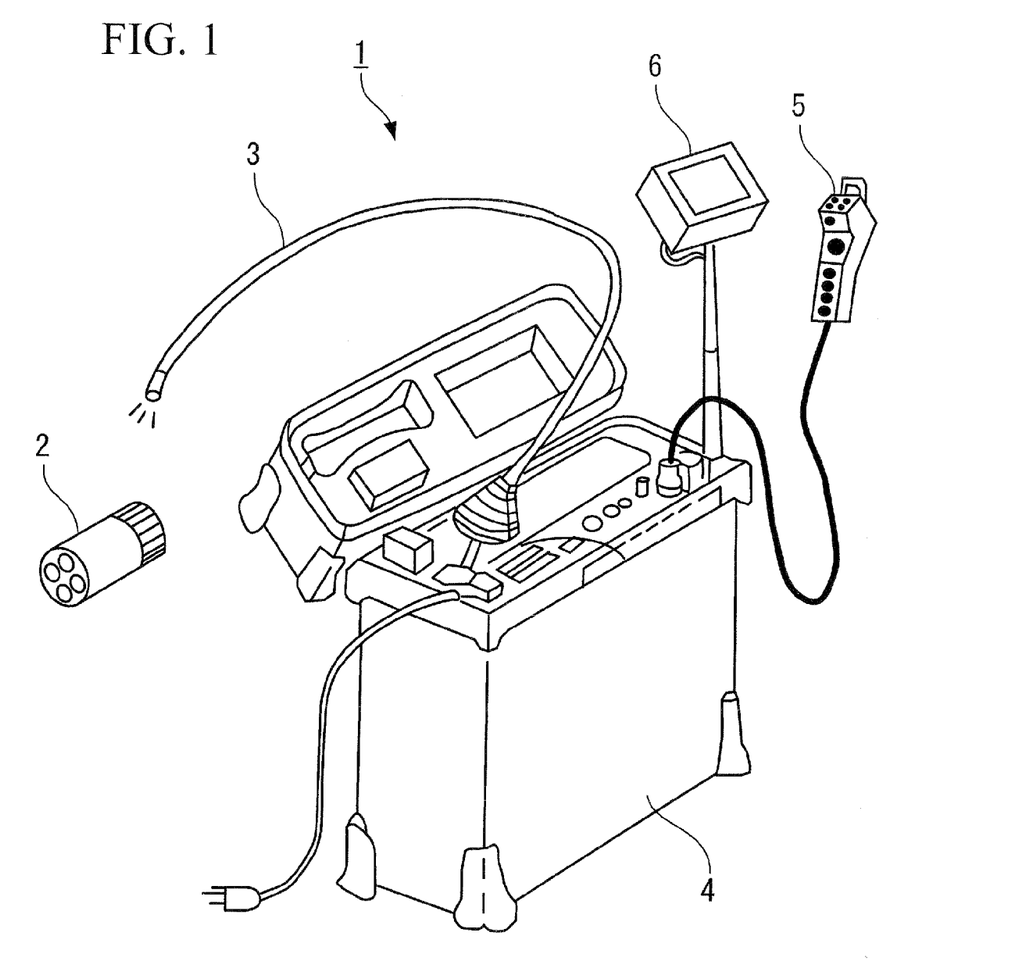
FIG. 1 is a perspective view showing the hardware design of the endoscope device according to the first embodiment of the present invention.

FIG. 1 is a perspective view showing the hardware design for the endoscope device 1 according to the first embodiment of the present invention. The endoscope device 1 is primarily composed of an optical adaptor for stereo measurement (referred to as "stereo optical adaptor" hereinafter) 2; an insertion part (referred to as "scope" hereinafter) 3 in which the stereo optical adaptor 2 can be attached to or released from the distal end thereof, a control unit 4 which houses the scope 3; a remote controller 5 for performing the required operations to execute control of various system-wide actions for the endoscope device 1; and a liquid crystal display 6 (referred to as "LCD" hereinafter) which is a display device for carrying out such displays as the endoscope image or the details of operation controls (processing menu, for example).

Figure 2:
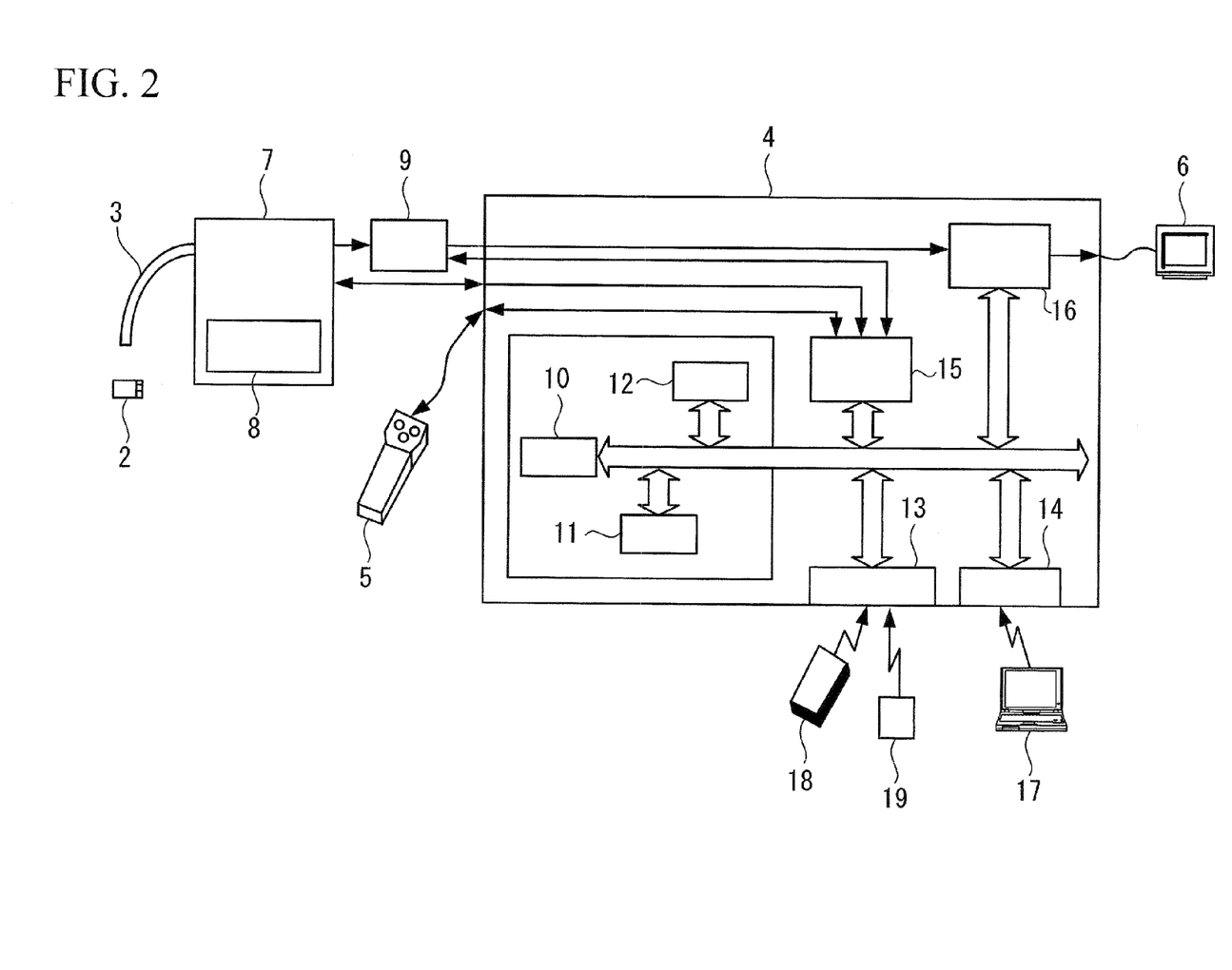
FIG. 2 is a block diagram showing the design of the endoscope device according to the first embodiment of the present invention.

Next, FIG. 2 is a block diagram showing the design of the endoscope device 1 according to the first embodiment. As shown in FIG. 2, the proximal part of the scope 3 is connected to the endoscope unit 7. This endoscope unit 7 is housed inside the control unit 4. Note that a light source for obtaining the illuminating light needed for capturing images, and an electrically driven bending device for electrically bending and driving a bending part, not shown in the figures, of the scope 3, are housed inside the endoscope unit 7. This electrically driven bending device includes a EEPROM 8 for recording the control parameters used for the bending driving and the parameters for correcting the distortion unique in the scope optical system (both referred to as simply "parameters" hereinafter).

An image pickup signal which is output from an image pickup element that is housed inside the scope 3 is input to a camera control unit 9 (CCU hereinafter) which is an image processor. This CCU 9 converts the input image pickup signal to a NTSC signal or other such image signal for example, and supplies this to the main circuits inside the control unit 4.

The main circuits housed inside the control unit 4 are composed of a CPU 10 (distortion correcting member), which combines a controller for executing various functions based on the main program, and a calculation processor (calculating member) which carries out calculations; a ROM 11; a RAM 12, a PC card interface (PC card I/F, hereinafter) 13; a USB interface (USB I/F hereinafter) 14; a RS-232 interface (RS-232C I/F hereinafter) 15; and an image signal processing circuit 16.

The RS-232C I/F 13 is connected to the CCU 9, the endoscope unit 7 and the remote controller 5, respectively. The remote controller 5 carries out control and operating directives for the CCU 9 and the endoscope unit 7. The RS-232C I/F 15 carries out the communications required for operating control of the CCU 9 and the endoscope unit 7 based on the manipulations of the remote controller 5.

The USB I/F 14 is an interface for electrically connecting the control unit 4 and a personal computer (referred to as PC, hereinafter) 17. When the control unit 4 and the PC 17 are connected via the USB I/F 14, control of various directives such as the directive for displaying the endoscopic image on the control unit 4, or image processing during measurements can also be carried out at the PC 17 side, and the input/output of data and control information needed for various processing between the control unit 4 and the PC 17 can be performed.

External recording medium such as a PCMCIA memory card 18 or Compact Flash (registered TM) memory card 19 are connected in a freely detachable manner to the PC card I/F 13. In other words, when an external recording medium is attached, the control unit 12 regenerates such data as the image information and control processing information that is recorded in the external recording medium, according to control by the CPU 10. This data is taken tip via the PC card I/F 13, or the data such as control processing information and image information can be supplied to and recorded in the memory card via the PC card I/F 13.

The image signal processing circuit 16 carries out synthesis processing of the image signal from the CCU 9 and the display signal that is based oil the operating memory generated by the control of CPU 10, so as to display a synthesized image in which the endoscopic image supplied from the CCU 9 and a graphic-based operating menu have been synthesized. The processing necessary to display this on the screen of the LCD 6 is then carried, and this is supplied to the LCD 6. As a result, a synthesized image consisting of the endoscopic image and the operating menu is displayed on the LCD 6. Note that it is also possible to employ the image signal processing circuit 16 to carry out processing to display just the endoscopic image, or to display an image such as the operating menu only.

The CPU 10 executes the programs stored inside the ROM 11, and performs system-wide operation control by controlling the various circuits so as to carry out the processing corresponding to the objective.

Note that the remote controller 5 is provided on its front face with at least a joy stick, a lever switch, a freeze switch, a store switch and a switch for executing measurements, which are not shown in the figures.

The endoscope device 1 shown in FIG. 1 and FIG. 2 has a hardware design that is the same for all of the embodiments explained below, including the first embodiment.

Figure 3:
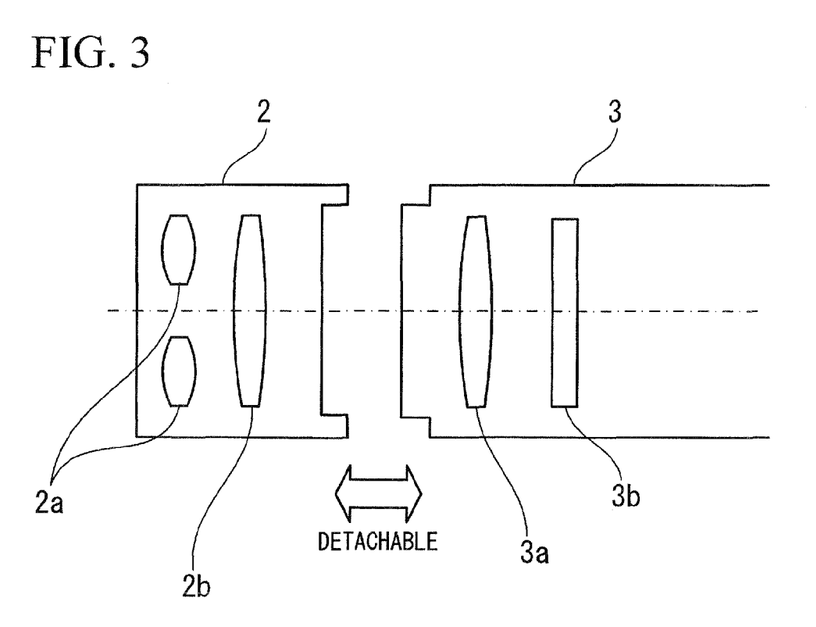
FIG. 3 is a conceptual view showing an abbreviated design of the stereo optical adaptor 2 and the optical system of the scope according to the first embodiment of the present invention.

Next, FIG. 3 is a conceptual view showing the abbreviated design of the stereo optical adaptor 2 and the optical system for the scope 3 according to the first embodiment. In this figure, the stereo optical adaptor 2 is for inputting two images having the required parallax for carrying out stereo measurements, and is composed mainly of paired right and left objective optical systems 2a and an adaptor side image transmitting optical system 2b. Further, the scope 3 is inserted into the area targeted for viewing and is used to capture images. The scope 3 is comprised mainly of an endoscope side image transmitting optical system 3a and an image pickup element (image pickup member) 3b. Note that the optical system of the scope 3 shown in FIG. 3 has a design which is the same for all of the embodiments explained below, including the first embodiment.

Figure 4:
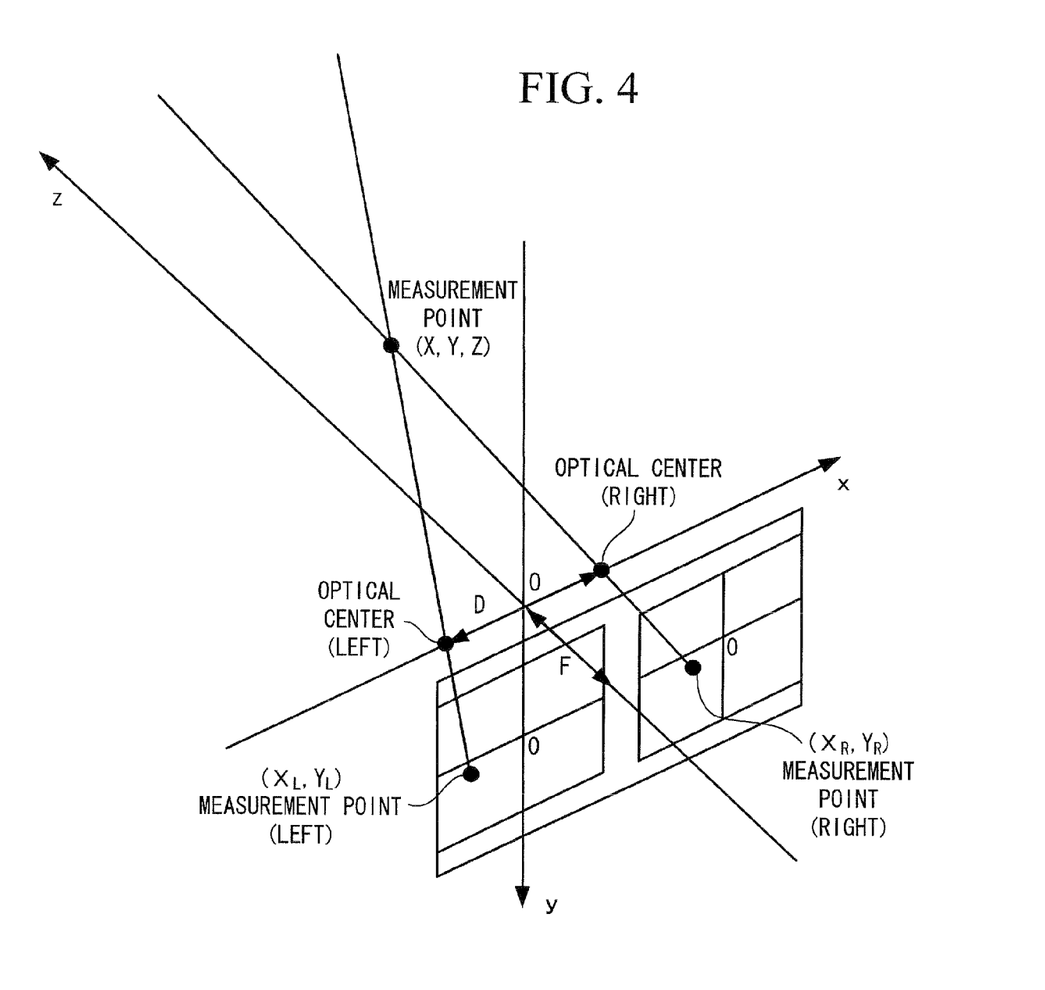
FIG. 4 is a conceptual view for explaining the enumeration method for three-dimensional coordinates using stereo measurements, according to the first embodiment of the present invention.

Next, FIG. 4 is a conceptual diagram for explaining the enumeration method for three-dimensional coordinates using stereo measurements according to the first embodiment. The coordinates of the measurement points on the image that is input in the optical systems on the left and right side of the scope 3 are defined as $(X_L, Y_L)$, $(X_R, Y_R)$ respectively, and the three-dimensional coordinates of the measurement point are defined as $(X, Y, Z)$. The distance between the centers of the left and right sided optical systems is defined as D, and the focal point distance is defined as F. The X, Y, and Z values are determined by the following Equation (1) using a triangulation method.

$$X = t \times X_R + D/2$$

$$Y = t \times Y_R$$

$$Z = t \times F$$

$$t = D/(X_L - X_R) \quad (1)$$

In the typical measurements, when the user inputs coordinates $(X_L, Y_L)$ of the measurement point on the left side of the screen, the coordinates $(X_R, Y_R)$ on the right side of the screen corresponding to point $(X_L, Y_L)$ are automatically determined using a conventionally known template matching method. As a result, the three-dimensional coordinates for the input measurement point are calculated. In order to carry out accurate stereo measurements, the following parameters should be provided accurately, optical data for correcting the distortion in the stereo optical adaptor and the scope optical system, and the distortion parameters of the scope.

Figure 5:
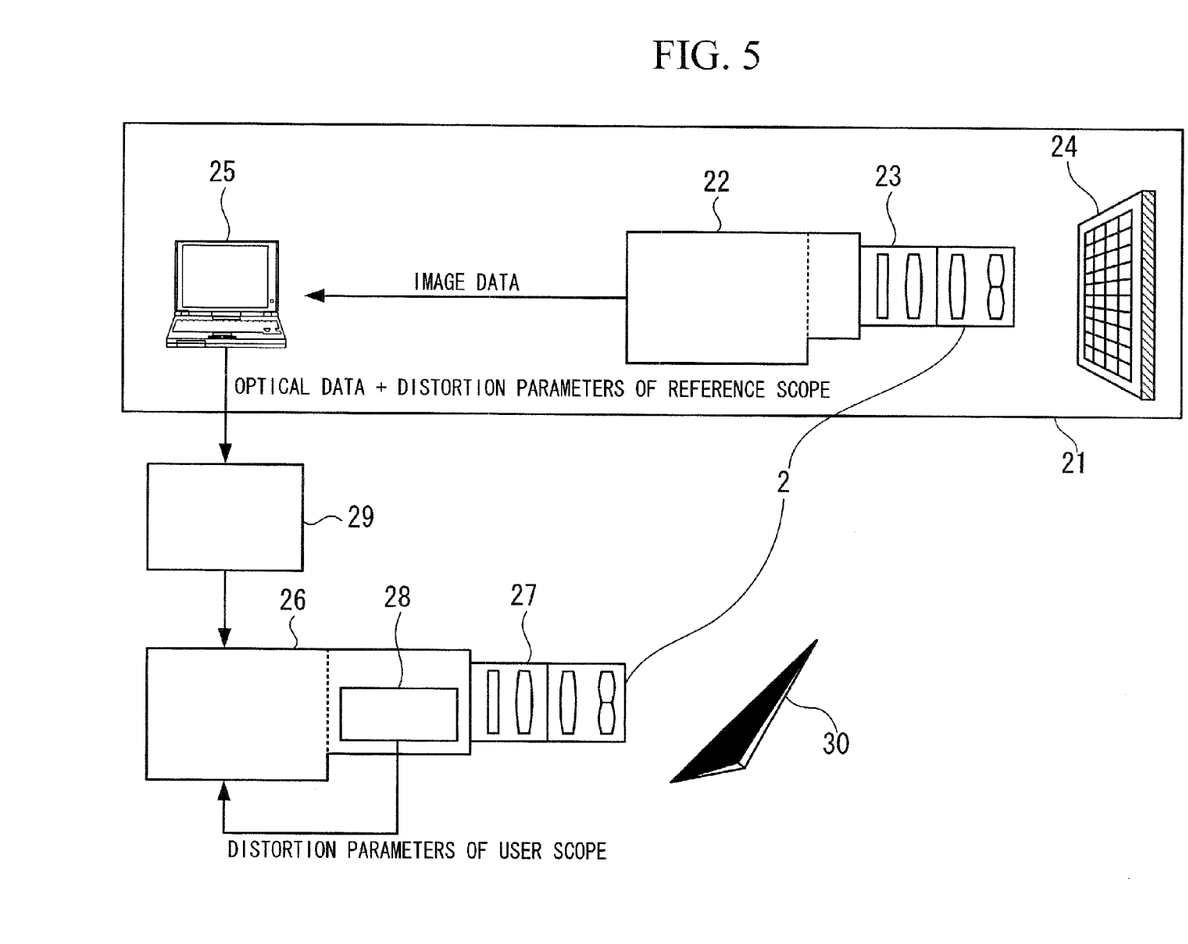
FIG. 5 is a block diagram for explaining the method for measuring the optical data of the stereo optical adaptor, according to the first embodiment of the present invention.

FIG. 5 is a block diagram for explaining the method for measuring the optical data of the stereo optical adaptor according to the first embodiment. The measurement of optical data is carried out during the production process by mounting a stereo optical adaptor 2 to a reference scope 23, which is a production equipment 21, capturing a lattice type chart 24 (specific target), and then performing the measurements of optical data using a PC 25 based on the captured image data. The details of the optical data are shown in the following (a) through (d).

(a) geometric distortion correction coefficient for two objective optical systems (b) focal length F for two objective optical systems (c) distance D between optical axes in two objective optical systems (d) attachment information how the stereo optical adaptor 2 is attached to the reference scope 23, i.e., position and rotation.

Figure 6:
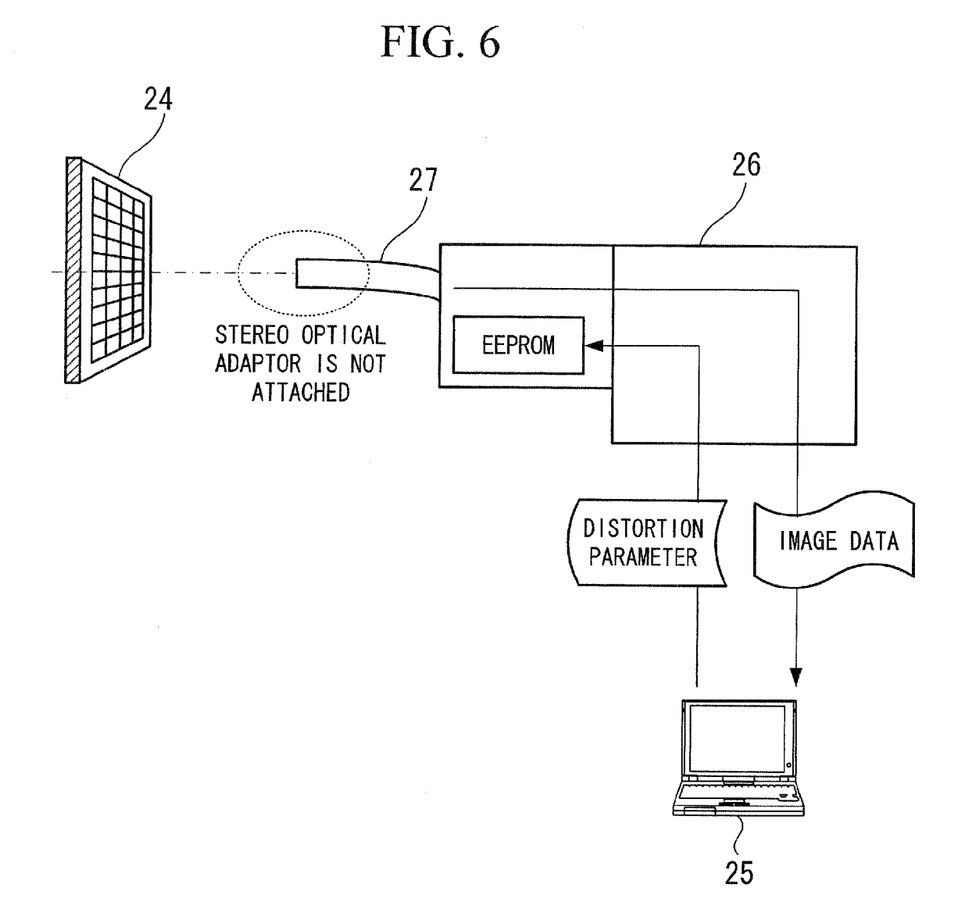
FIG. 6 is a block diagram for explaining the method for measuring the distortion parameters of the reference scope and the distortion parameters of the user scope, according to the first embodiment of the present invention.

FIG. 6 is a block diagram for explaining the method for measuring (e) the distortion parameters of the reference scope 23, and (f) the distortion parameters of the user scope 27 that is mounted to the endoscope (referred to as "user scope" hereinafter) 26 that is actually employed by the user. The design shown in FIG. 6 is an equipment for measuring the distortion parameters of the user scope 27. The lattice-type chart 24 is captured from a predetermined distance, in an arrangement in which the stereo optical adaptor 2 is not attached to the user scope 27. PC 25 takes up an image data of the lattice-type chart 24, and the distortion parameters (f) of the user scope 27 are calculated using image processing. The distortion parameters to be measured include the distortion center and the magnification. The measured distortion parameters of the user scope 27 are recorded in the EEPROM (second recording medium) 28 that is mounted inside the user endoscope 26. Note that while not specifically shown in the figures, the method for measuring the (e) distortion parameters of the reference scope 23 is the same as in the case of the user scope 27 previously described above.

Referring back to FIG. 5, the optical data of the above (a)~(d) and the (e) distortion parameter of the reference scope 23 are recorded in the memory card as the optical data card 29 (first recording medium). As a result, the optical data card 29 is associated with the stereo optical adaptor 2.

After the optical data is measured, the stereo optical adaptor 2 is attached to the user scope 27. As a result, it is possible to carry out stereo measurements using processes (1)~(9) shown next.

(1) Reading the optical data of (a)~(d) above and the (e) distortion parameters of the reference scope 23 from the optical data card 29.

(2) Capturing white colored objects are by the user endoscope 26.

(3) Detecting how the stereo adaptor 2 is attached to the user endoscope 27, i.e., position and rotation.

(4) Calculating the difference of the distortion parameters between the reference scope 23 and the user scope 27 read out from the EEPROM 28.

(5) Modifying the optical data with the data of (3) and (4) above, and generating the conversion table for correcting distortion of the user scope 27 and the stereo optical adaptor 2. This optical data and the conversion table are recorded in a memory card, not shown, to serve as an environment data card.

(6) Capturing the object 30 to be measured with the user endoscope 26.

(7) Correcting the distortion of the image picked up in (6) above based on the conversion table generated in (5) above.

(8) Calculating the three-dimensional coordinates of an user-specified point using the method above based on the image (7) above.

(9) Carrying out stereo measurements based on the three-dimensional coordinates that were determined in (8) above.

Note that in the second and subsequent stereo measurements, it is acceptable to read out the environment data card created in (5) above. Thus, processes (1) through (5) can be skipped.

The distortion correction method in the first embodiment will now be explained. This distortion correction method consists of a first distortion correction for correcting the distortion in the objective optical system 2a in FIG. 3, and a second distortion correction for correcting the distortion in the synthesized image transmitting optical system which is the combination of the endoscope side image transmitting optical system 3a and the adaptor side image transmitting optical system 2b. These distortion corrections are carried out using coordinate conversion. The coordinate conversion of the first distortion correction and the second distortion correction are as shown in the following equations (2)~(13).

<Second Distortion Correction>

$$f_{2x}(u,v)=k_{2x}(a_{200}+a_{212}uv^2+a_{214}uv^4+a_{216}uv^6+a_{230}u^3+a_{232}u^3v^2+a_{234}u^ev^4+a_{250}u^5+a_{252}u^5v^2+u_{270}u^7)+c_{2x} \quad (2)$$

$$f_{2y}(u,v)=k_{2y}(b_{200}+b_{221}u^2v+b_{241}u^4v+b_{261}u^6v+b_{203}v^3+b_{223}u^2v^3+b_{243}u^4v^3+b_{205}v^5+b_{225}u^2v^5+b_{207}u^7)+c_{2y} \quad (3)$$

$$x_2=f_{2x}(x-c_{2x},y-c_{2y}) \quad (4)$$

$$y_2=f_{2y}(x-c_{2x},y-c_{2y}) \quad (5)$$

]<First Distortion Right Correction>

$$f_{Rx}(u,v)=k_{Rx}(a_{R00}+a_{R12}uv^2+a_{R14}uv^4+a_{R16}uv^6+a_{R30}u^3+a_{R32}u^3v^2+a_{R34}u^3v^4+a_{R50}u^5+a_{R52}u^5v^2+a_{R70}u^7)+c_{Rx} \quad (6)$$

$$f_{Ry}(u,v)=k_{Ry}(b_{R00}+b_{R21}u^2v+b_{R41}u^4v+b_{R61}u^6v+b_{R03}v^3+b_{R23}u^2v^3+b_{43}u^4v^3+b_{R05}v^5+b_{R25}u^2v^5+b_{R07}u^7)+c_{Ry} \quad (7)$$

$$x_R'=f_{Rx}(x_2-c_{Rx},y_2-c_{Ry}) \quad (8)$$

$$y_R'=f_{Ry}(y_2-c_{Rx},y_2-c_{Ry}) \quad (9)$$

<First Distortion Right Correction>

$$f_{Lx}(u,v)=k_{Lx}(a_{L00}+a_{L12}uv^2+a_{L14}uv^4+a_{L16}uv^6+a_{L30}u^3+a_{L32}u^3v^2+a_{L34}u^3v^4+a_{L50}u^5+a_{L52}u^5v^2+a_{L70}u^7)+c_{Lx} \quad (10)$$

$$f_{Ly}(u,v)=k_{Ly}(b_{L00}+b_{L21}u^2v+b_{L41}u^4v+b_{L61}u^6v+b_{L03}v^3+b_{L23}u^2v^3+b_{L43}u^4v^3+b_{L05}v^5+b_{L25}u^2v^5+b_{L07}u^7)+c_{Ly} \quad (11)$$

$$x_L'=f_{Lx}(x_2-c_{Lx},y_2-c_{Ly}) \quad (12)$$

$$y_L'=f_{Ly}(x_2-c_{Lx},y_2-c_{Ly}) \quad (13)$$

Where, in Equations (2)~(13): x,y are the coordinates before correction; $x_R',y_R'$ are the coordinates on the right screen after correction; $x_L',y_L'$ are the coordinates on the left screen after correction; $c_{2x},c_{2y}$ are coordinates of the second distortion; $c_{Rx},c_{Ry}$ are the coordinates of the right first distortion center; $c_{Lx},c_{Ly}$ are the coordinates of the left first distortion center; $k_{2x},k_{2y}$, $a_{2ij},b_{2ij}$ are the coefficients to correct the second distortion; $k_{Rx},k_{Ry}$, $a_{Rij},b_{Rij}$ are the coefficients to correct the right first distortion; and $k_{Lx},k_{Ly}$, $a_{Lij},b_{Lij}$ are the coefficients to correct the left first distortion.

The coefficients $a_{2ij}$, $b_{2ij}$, $a_{Rij}$, $a_{Lij}$, $b_{Lij}$, $c_{2x}$, $c_{2y}$, $c_{Rx}$, $c_{Ry}$, $c_{Lx}$, $c_{Ly}$, are determined according to the linearity of the lattice image. The $k_{2x}$, $k_{2y}$, $k_{Rx}$, $k_{Ry}$, $k_{Lx}$, and $k_{Ly}$ are the coefficients which fit the magnification of two images which are the function of the focal length $f_R, f_L$.

The parameters above are included in the optical data which is generated by combining the reference scope 23 and the stereo optical adaptor 2. In order to correct a difference between the reference scope 23 and the user scope 27, $m_m/m_u$ (where $m_m$ is the magnification of the reference scope 23 and $m_u$ is the magnification of the user scope 27) is multiplied to the coefficients $k_x$, $k_y$, corresponding to the magnification of the synthesized image transmitting optical system, and the coordinates $c_x,c_y$ corresponding to the center of distortion of the synthesized image transmitting optical system are corrected based on $c_{mx}$, $c_{my}$, $c_{ux}$, $c_{uy}$ (where $c_{mx}$, $c_{my}$ are the distortion centers of the image transmitting optical system on the endoscope side in the reference endoscope 23, and $c_{ux}$, $c_{uy}$ are the distortion centers of the image transmitting optical system on the endoscope side in the user endoscope 27). As a result, distortion correction can be carried out more accurately, making it possible to improve the precision of the stereo measurements.

A': Modification of First Embodiment

A modification of the first embodiment will now be explained. The distortion correction method in this modification consists of a first distortion correction for correcting the distortion in the objective optical system 2a in FIG. 3, a second distortion correction for correcting the distortion in the adaptor side image transmitting optical system 2b in FIG. 3, and a third distortion correction for correcting the distortion in the endoscope side image transmitting optical system 3a in FIG. 3.

The coordinate conversion for the first distortion correction is equivalent to that of Equations (6) through (13). The coordinate conversion for the third distortion correction is as shown in Equations (14)~(17) shown below.

$$f_{3x}(u,v) = k_{3x}(a_{300} + a_{313}uv^2 + a_{314}uv^4 + a_{316}uv^6 + a_{330}u^3 + a_{332}u^3v^2 + a_{334}u^3v^2 + a_{334}u^3v^4 + a_{350}u^5 + a_{353}u^5v^2 + a_{370}u^7) + c_{3x} \quad (14)$$

$$f_{3y}(u,v) = k_{3y}(b_{300} + b_{321}u^2v + b_{341}u^4v + b_{361}u^6v + b_{303}v^3 + b_{323}u^2v^3 + b_{343}u^4v^3 + b_{305}v^5 + b_{325}u^2v^5 + b_{307}v^7) + c_{3y} \quad (15)$$

$$x_3 = f_{3x}(x - c_{3x}, y - c_{3y}) \quad (16)$$

$$y_3 = f_{3y}(x - c_{3x}, y - c_{3y}) \quad (17)$$

The third distortion coordinate conversion is as shown in Equations (2)~(3) and Equations (18)~(19) shown below.

$$x_2 = f_{2x}(x_3 - c_{2x}, y_3 - c_{2y}) \quad (18)$$

$$y_2 = f_{2y}(x_3 - c_{2x}, y_3 - c_{2y}) \quad (19)$$

Where, in Equations (14)~(19), $c_{3x}$, $c_{3y}$ are the third distortion center coordinates, and $k_{3x}$, $k_{3y}$, $a_{3ij}$, $b_{3ij}$ are the third distortion correction coefficients;

The specific procedure for correcting distortion in these modifications is as follows. First, optical data in which the distortion in the optical system of the reference scope 23 has been corrected is measured. Namely, as shown in FIG. 5, the distortion in the optical system of the reference scope 23 is corrected based on the Equations (14)~(17), with respect to the image data captured after attaching the stereo optical adaptor 2 to the reference scope 23 which is installed in the reference endoscope 22. Next, optical data is measured based on the image data after distortion correction. The measured optical data is recorded in the optical data card 29.

The coordinates of the third distortion center and the coefficients to correct the third distortion in Equations (14)~(17) are the distortion parameters of the reference scope 23. The distortion parameters of the reference scope 23 are measured in advance using the same method as that described above, and are recorded in the optical data card 29. The optical data measured with the image data in which the distortion of the optical system of the reference scope 23 has been corrected are comprised of the parameters for correcting the distortion of only the stereo optical adaptor 2. The coordinates of the first distortion centers (first distortion right center coordinates, first distortion left center coordinates), the coefficients to correct the first distortion correction (first distortion right correction coefficient, first distortion left correction coefficient), the coordinates of the second distortion centers, and the coefficients to correct the second distortion are included in the optical data.

In the user endoscope 26 in which the stereo optical adaptor 2 is attached to the user scope 27, distortion correction can be carried out as follows. The distortion parameters of the user scope 27 are measured in advance using the same method as described above, and are recorded in the EEPROM 28. The coordinates of the third distortion center and the coefficients to correct the third distortion are included in the distortion parameters of the user scope 27. The distortion parameters of the user scope 27 are read out from the EEPROM 28, and the third distortion correction can be carried out based on these parameters and the Equations (14)~(17).

The optical data is read out from the optical data card 29, and the first distortion correction and the second distortion correction can be carried out based on this and the Equations (2)~(3), (6)~(13), and (18)~(19). Using the distortion correction method according to this modification enables a more accurate correction of image distortion as compared to the distortion correction method according to the first embodiment described above.

B. Second Embodiment

The second embodiment of the present invention will now be explained.

Figure 7:
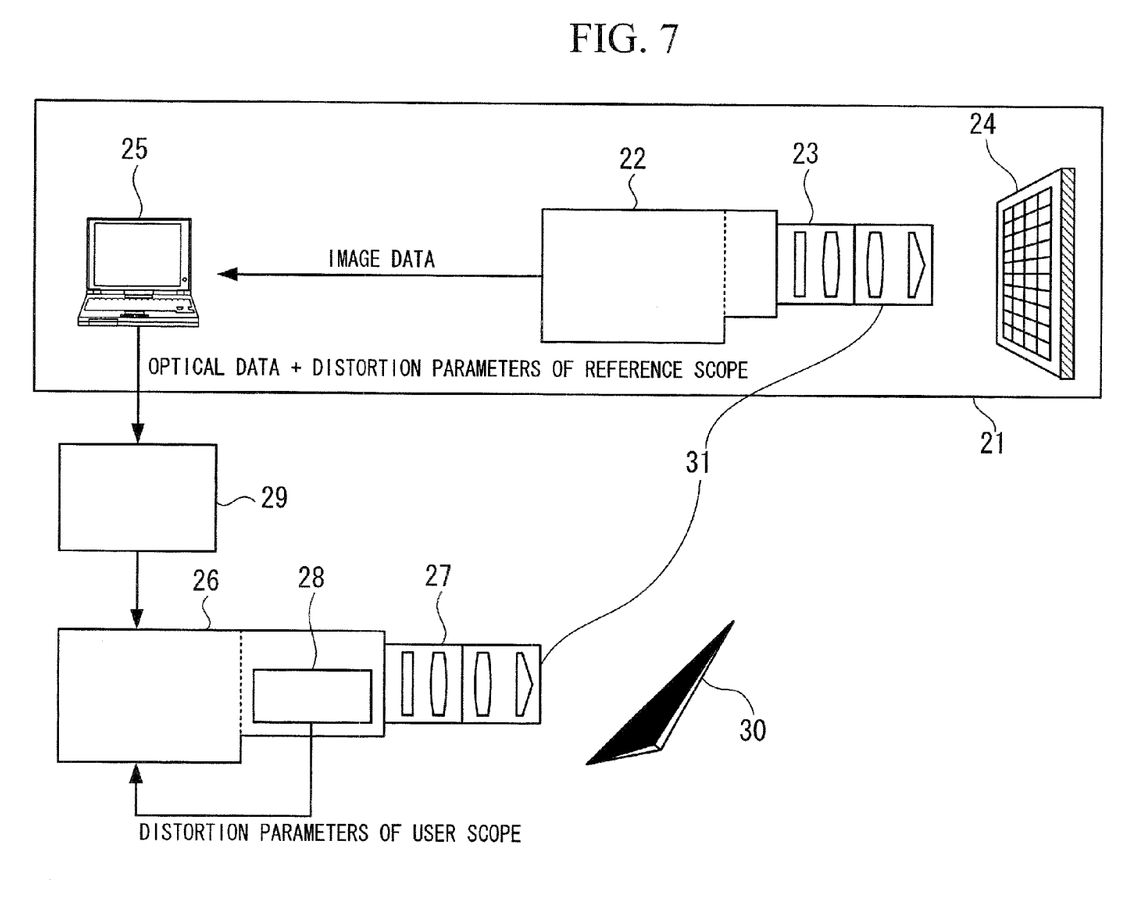
FIG. 7 is a block diagram for explaining the method for measuring the optical data of the stereo optical adaptor according to the second embodiment of the present invention.
Figure 8:
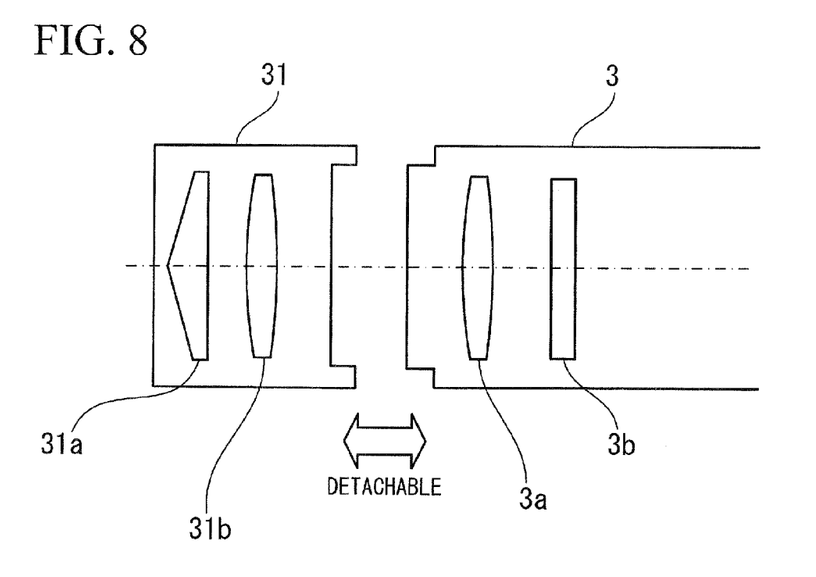
FIG. 8 is a conceptual view showing the abbreviated design of the stereo optical adaptor 2 and the optical system of the scope 3, according to the second embodiment of the present invention.

FIG. 7 is a block diagram for explaining the method for measuring the optical data of the stereo optical adaptor according to the second embodiment. The endoscope device according to this second embodiment is provided with a stereo optical adaptor 31 as shown in FIG. 8, with the remainder being equivalent to that of the first embodiment. Namely, the stereo optical adaptor 31 according to the second embodiment consists of an objective optical system 31a in the form of a single prism and an adaptor side image transmitting optical system 31b, in order to input two image having a parallax.

Figure 9:
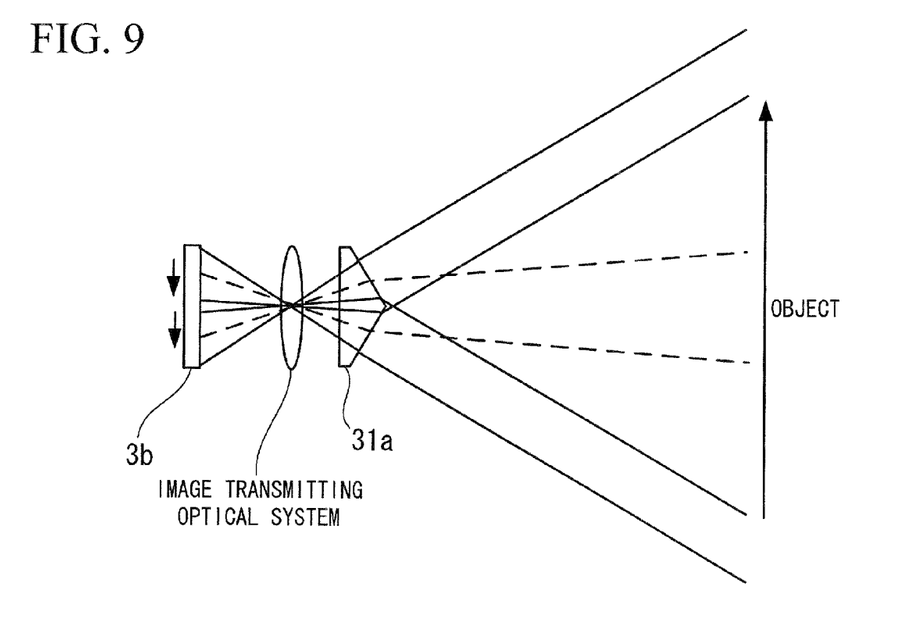
FIG. 9 is a conceptual view for explaining the enumeration method for three-dimensional coordinates using stereo measurements, according to the second embodiment of the present invention.

As shown in FIG. 9, the same object can be picked up from different viewpoints using the prism shaped objective optical system 31a and the image transmitting optical system (endoscope side image transmitting optical system 3a, adaptor side image transmitting optical system 31b). Accordingly, even in the case where using an optical system that employs a prism or other such typical element for the optical element, the distortion correction can be carried out more accurately by correcting the optical data based on the differences between the reference scope 23 and the user scope 27. Thus, the precision of the stereo measurements can be improved.

C. Third Embodiment

A third embodiment of the present invention will now be explained.

Figure 10:
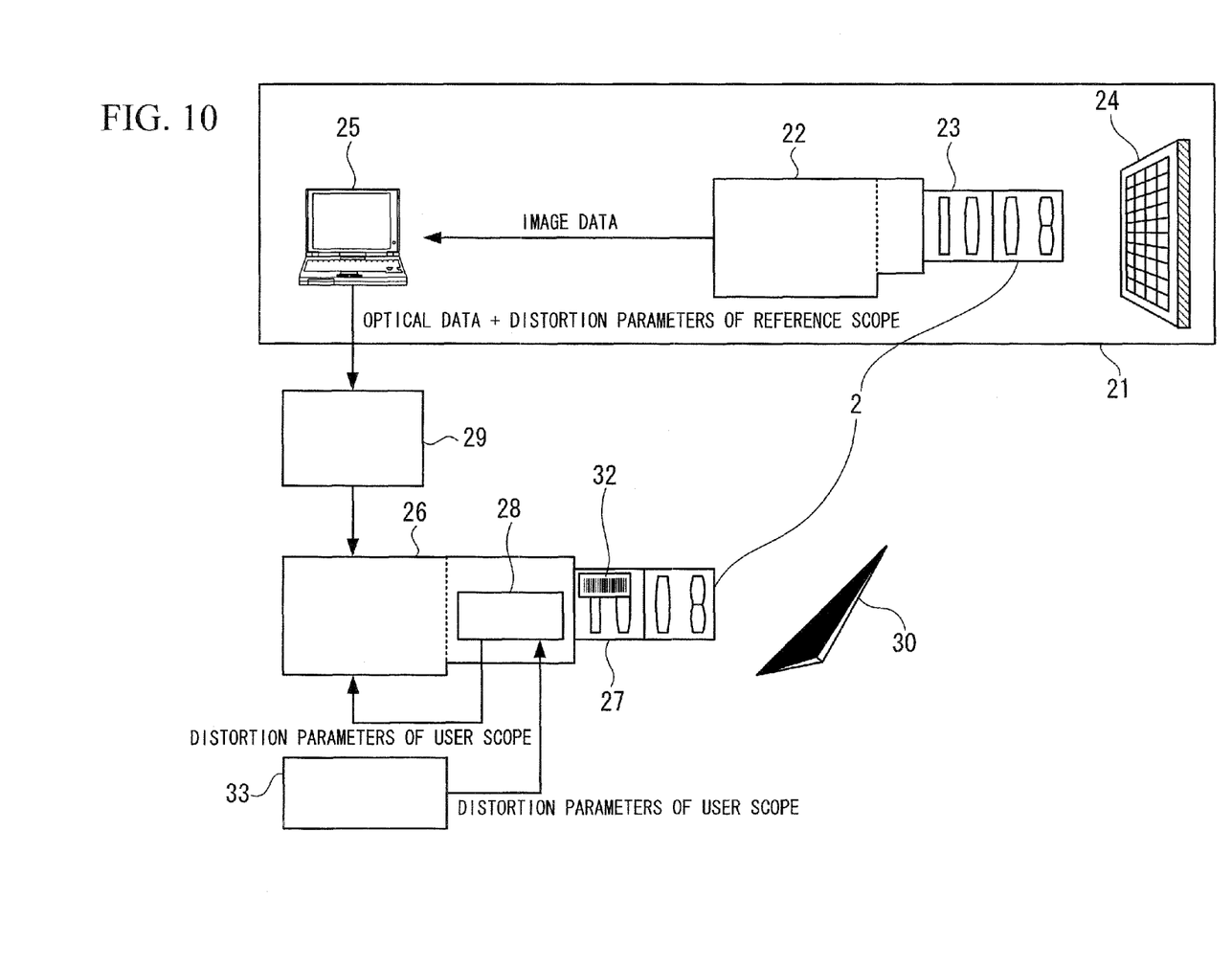
FIG. 10 is a block diagram for explaining the method for measuring the optical data of the stereo optical adaptor according to the third embodiment of the present invention.

FIG. 10 is a block diagram for explaining the method for measuring the optical data of the stereo optical adaptor according to a third embodiment of the present invention. The endoscope device according to the third embodiment is provided with a barcode 32 on the user scope 27 which records the ID of the user scope 27, and is designed to record the distortion parameters of the user scope 27 in the EEPROM 28 by referencing from the distortion parameter database 33. The remainder of the endoscope device is equivalent to that of the first embodiment.

The data recorded in the EEPROM 28 can disappear due to electrical noise or other malfunction. Further, in the case where it is necessary to exchange the scope itself because it is damaged, etc., the data recorded in the EEPROM 28 will need to be renewed. In this case (i.e., in the case where readout of the distortion parameters of the user scope 27 fails), various methods may be considered in order to re-record the data, including:

referencing and recording a ledger for the distortion parameters that was previously measured measuring and recording the distortion parameters again However, referencing past data is problematic in that it is time consuming and troublesome.

Thus, the third embodiment employs the following means to resolve this problem.

(1) Attach the barcode 32 in which the ID of the user scope 27 is recorded to the user scope 27

(2) In the case where it is necessary to write to the EEPROM 28, read out the corresponding distortion parameters of the user scope 27 from the distortion parameter data base 33 based on the barcode ID. Note that the distortion parameter data base 33 is the database which records the distortion parameters of the user scope 27 that were measured during production.

(3) Record these distortion parameters in the EEPROM 28

As a result, even if the data in the EEPROM 28 disappears and needs to be renewed, it is possible to record the data easily and over a short period of time by referencing the distortion parameter data base 33. Note that it is also acceptable to use an ID tag which records the ID of the user scope 27, in place of a barcode 32.

D. Fourth Embodiment

Next, a fourth embodiment of the present invention will now be explained.

Figure 11:
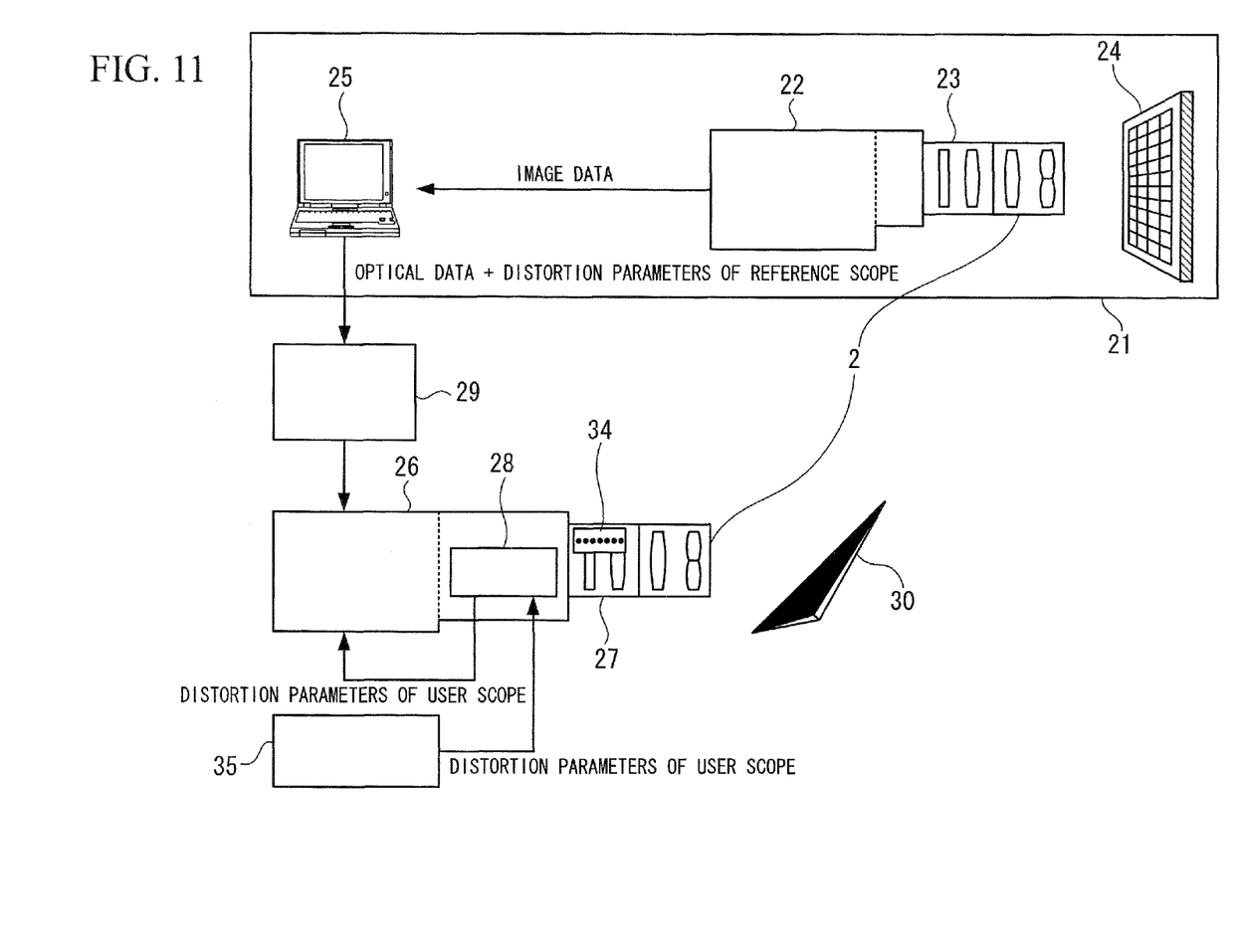
FIG. 11 is block diagram for explaining the method for measuring the optical data of the stereo optical adaptor according to the fourth embodiment of the present invention.

FIG. 11 is a block diagram for explaining the method for measuring the optical data of the stereo optical adaptor according to a fourth embodiment of the present invention. As shown in FIG. 11, the endoscope device according to the fourth embodiment is configured by affixing a printed sheet 34 on which the distortion parameters of the user scope 27 are recorded to the user scope 27, and recording this in the EEPROM 28 using the distortion parameter input device 35 of the user scope 27. The remainder of the endoscope device is equivalent to the first embodiment.

As explained above, the data recorded in EEPROM 28 can disappear due to electrical noise or other damage. Further, in the case where it is necessary to exchange the scope itself because it is damaged, etc., the data recorded in the EEPROM 28 will need to be renewed. In this case (i.e., in the case where readout of the distortion parameters of the user scope 27 fails), various methods may be considered in order to re-record the data, including:

referencing and recording a ledger of the distortion parameters that was previously measured measuring and recording the distortion parameters again However, referencing past data is problematic in that it is time consuming and troublesome.

Thus, the fourth embodiment employs the following means to resolve this problem.

(1) Attach the printed sheet 34 recording the distortion parameters of the user scope 27 to the user scope 27

(2) In the case where it is necessary to write to the EEPROM 28, record these distortion parameters in the EEPROM 28 from the input device 35 based on the printed sheet 34

As a result, even if the data in the EEPROM 28 disappears and needs to be renewed, it is possible to record the data easily and over a short period of time by referencing the printed sheet 34 on which the distortion parameters of the user scope 27 measured previously are recorded.

In the above-described first through fourth embodiments, the distortion of the image generated by the difference in the optical properties of the reference scope and the user scope can be more accurately corrected. Further, the accuracy of the stereo measurements can be improved as a result.

Note that in the preceding embodiments, the course of the serial processing by the CPU 10 is recorded in the recording medium which can be read out from the computer in a program form. By the computer reading out and executing this program, the above processing can be carried out. In other words, with regard to the various processing means or processor in the CPU 10, the central calculation processing device, such as a CPU, reads out the program in the main recording device such as a ROM or RAM, and executes the manipulation and calculation processing of information.

The recording medium that can be read out from the computer includes such examples as an electromagnetic disk, photoelectromagnetic disk, CD-ROM, DVD-ROM, semiconductor memory or the like. Further, it is acceptable for the computer program to be transmitted to the computer via communication circuits, and the computer which receives this communication to execute this program.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope device in which a portion of an optical system can be changed using an optical adaptor, the endoscope device comprising:

an image pickup member configured for capturing an image that is input from the optical system, wherein the optical system is operable in at least two configurations including (i) a first configuration in which the optical adapter is combined with a reference scope, and (ii) a second configuration in which the optical adaptor is combined with a user scope;

a first recording medium that records distortion parameters of the reference scope, the distortion parameters of the reference scope indicating optical properties of the reference scope;

a second recording medium that records distortion parameters of the user scope, the distortion parameters of the user scope indicating optical properties of the user scope; and a distortion correcting member configured for correcting distortion in the image captured by the image pickup member when the optical system is operated in the second configuration, based on (i) optical data for correcting distortion in the optical system having the first configuration, (ii) the distortion parameters of the reference scope, and (iii) the distortion parameters of the user scope;

wherein the second recording medium is provided inside the endoscope device, or is provided to an internal part of the user scope that is releasable from the endoscope device.

2. The endoscope device according to claim 1, wherein the first recording medium records the optical data for correcting distortion in the optical system having the first configuration.

3. The endoscope device according to claim 1, wherein the first recording medium records optical data for correcting distortion in an optical system of the optical adaptor.

4. The endoscope device according to claim 1, wherein the first recording medium records first recognition information for recognizing at least the reference scope, so that the distortion parameters of the reference scope can be referenced from another recording medium.

5. The endoscope device according to claim 1, wherein the second recording medium comprises a semiconductor memory in which at least the distortion parameters of the user scope are recorded.

6. The endoscope device according to claim 1, wherein the second recording medium comprises a medium in which at least the distortion parameters of the user scope are printed or copied to permit recognition.

7. The endoscope device according to claim 1, wherein the second recording medium records second recognition information for recognizing at least the user scope, so that the distortion parameters of the user scope can be referenced from another recording medium.

8. The endoscope device according to claim 1, further comprising a measuring member configured for measuring an object based on the image which has been corrected for distortion by the correcting member.

9. The endoscope device according to claim 8, wherein the optical adaptor is provided with an optical element for performing image pickup from different viewpoints using the image pickup member, and the measuring member performs three-dimensional measurements using triangulation of the image captured from different viewpoints by said image pickup member via the optical element.

10. The endoscope device according to claim 9, wherein the optical element has a plurality of optical paths.

11. The endoscope device according to claim 10, wherein the distortion parameters of the reference scope include a distortion center for the reference scope, and the distortion parameters of the user scope include a distortion center for the user scope.

12. The endoscope device according to claim 1, wherein the distortion parameters of the reference scope include a magnification for the reference scope, and the distortion parameters of the user scope include a magnification for the user scope.

13. An endoscopic image distortion correction method for correcting distortion in an image captured by an endoscope device in which a portion of an optical system is changeable, the optical system being operable in at least two configurations including (i) a first configuration in which an optical adaptor is combined with a reference scope, and (ii) a second configuration in which the optical adapter is combined with a user scope, the method comprising:
  reading in optical data for correcting distortion in the optical system having the first configuration, the optical data being stored in a first recording medium;
  reading in distortion parameters of the reference scope, wherein the distortion parameters of the reference scope indicate optical properties of the reference scope and are stored in the first recording medium;
  reading in distortion parameters of the user scope, wherein the distortion parameters of the user scope indicate optical properties of the user scope and are stored in a second recording medium; and
  correcting the distortion in the image captured by the endoscope device with the optical system having the second configuration, based on (i) the optical data for correcting distortion in the optical system having the first configuration, (ii) the distortion parameters of the reference scope, and (iii) the distortion parameters of the user scope;
  wherein the second recording medium is provided inside the endoscope device, or is provided to an internal part of the user scope that is releasable from the endoscope device.

14. The endoscopic image distortion correction method according to claim 13, wherein correcting the distortion in the image captured by the endoscope device includes processing to correct distortion in the captured image based only on the optical data, for a case in which reading in of the distortion parameters of one of the reference scope and the user scope has failed.

* * * * *